United States Patent
Malle et al.

(10) Patent No.: US 10,092,490 B2
(45) Date of Patent: Oct. 9, 2018

(54) METHOD FOR STRAIGHTENING KERATINOUS FIBRES USING HEATING MEANS AND AN AMIDE

(75) Inventors: Gérard Malle, Villiers S/Morin (FR); Anne-Claude Dublanchet, Antony (FR); Philippe Barbarat, Bois-Colombes (FR)

(73) Assignee: L'Oreal, Paris (FR)

( * ) Notice: Subject to any disclaimer, the term of this patent is extended or adjusted under 35 U.S.C. 154(b) by 1069 days.

(21) Appl. No.: 12/301,973

(22) PCT Filed: May 23, 2007

(86) PCT No.: PCT/FR2007/000869
§ 371 (c)(1),
(2), (4) Date: Mar. 19, 2010

(87) PCT Pub. No.: WO2007/135296
PCT Pub. Date: Nov. 29, 2007

(65) Prior Publication Data
US 2010/0163070 A1    Jul. 1, 2010

Related U.S. Application Data

(60) Provisional application No. 60/814,530, filed on Jun. 19, 2006.

(30) Foreign Application Priority Data

May 24, 2006   (FR) ...................... 06 51913

(51) Int. Cl.
*A61K 8/42* (2006.01)
*A61K 8/49* (2006.01)
*A61Q 5/04* (2006.01)

(52) U.S. Cl.
CPC .............. *A61K 8/42* (2013.01); *A61K 8/4913* (2013.01); *A61Q 5/04* (2013.01); *A61K 2800/24* (2013.01)

(58) Field of Classification Search
None
See application file for complete search history.

(56) References Cited

U.S. PATENT DOCUMENTS

| | | | | |
|---|---|---|---|---|
| 4,220,167 A * | 9/1980 | Newell | .......................... | 132/209 |
| 4,374,125 A * | 2/1983 | Newell | .................. | A61K 8/345 424/70.14 |
| 5,154,918 A | 10/1992 | Maignan et al. | | |
| 5,609,860 A | 3/1997 | Tabata et al. | | |
| 5,661,118 A * | 8/1997 | Cauwet et al. | ................ | 510/126 |
| 5,957,140 A | 9/1999 | McGee | | |
| 5,964,227 A * | 10/1999 | Collin | .......................... | 132/209 |
| 5,968,286 A * | 10/1999 | Crudele et al. | .................. | 134/42 |
| 6,517,822 B1 * | 2/2003 | Buck | .......................... | 424/70.2 |
| 2005/0013786 A1 * | 1/2005 | Sabbagh et al. | ........... | 424/70.13 |
| 2005/0229336 A1 * | 10/2005 | Fondin | .................... | A61K 8/23 8/405 |
| 2006/0013784 A1 | 1/2006 | Nordhoff et al. | | |
| 2006/0083702 A1 | 4/2006 | Fondin et al. | | |
| 2007/0009462 A9 | 1/2007 | Malle et al. | | |

FOREIGN PATENT DOCUMENTS

| | | |
|---|---|---|
| DE | 35 35 351 A1 | 4/1987 |
| DE | 3535351 * | 10/1995 |
| EP | 0 465 342 B1 | 1/1992 |
| EP | 1369103 | 10/2003 |
| EP | 1 468 667 B1 | 10/2004 |
| EP | 1 570 834 A1 | 9/2005 |
| EP | 1 584 327 A1 | 10/2005 |
| JP | 1-503297 | 11/1989 |
| JP | 7-316025 | 12/1995 |
| JP | 9-301831 | 11/1997 |
| JP | 2002-356408 | 12/2002 |
| JP | 2005-290004 | 10/2005 |
| JP | 2005-298502 | 10/2005 |
| WO | WO 88/00186 | 1/1988 |

OTHER PUBLICATIONS

Lehman, Sodium Requirements and Dietary Sources, http://nutrition.about.com/od/mineralglossary/g/sodiumglossary.htm, retrieved online on Jul. 2, 2014.*
PH Balanced Shampoo for All Types of Hair, http://sulfatefreeshampoobrandsinfo.com/ph-balanced-shampoo., retrieved online on Jul. 2, 2014.*
SciFinder, Sodium Pyroglutamate, retrieved online on Jul. 2, 2014.*
International Search Report for PCT/FR2007/000869, dated Oct. 25, 2007.
Database WPI Week 200346, Derwent Publications Ltd., London, GB; AN 2003-485967, XP002454409.
English language abstract of DE 35 35 351 A1, Apr. 9, 1987.
English translation of Japanese Office Action (Notice of Reasons for Rejection) for JP Application No. 2009-511548 (3 pages).
Patent Abstract of Japan of JP 7-316025.
Patent Abstract of Japan of JP 9-301831.
Patent Abstract of Japan of JP 2002-356408.
Patent Abstract of Japan of JP 2005-290004.
Patent Abstract of Japan of JP 2005-298502.

* cited by examiner

*Primary Examiner* — Jennifer A Berrios
(74) *Attorney, Agent, or Firm* — The Marbury Law Goup, PLLC

(57) ABSTRACT

The invention concerns a method for straightening keratinous fibers including: (i) a step of applying on the keratinous fibers a hair straightening composition containing at least one cyclic or linear amide, (ii) a step of increasing the temperature of the keratinous fibers, using heating means, to a temperature ranging between 110 and 250° C.

10 Claims, No Drawings

METHOD FOR STRAIGHTENING KERATINOUS FIBRES USING HEATING MEANS AND AN AMIDE

CROSS REFERENCE TO RELATED APPLICATIONS

This application is a national phase application based on PCT/FR2007/000869, filed May 23, 2007, which claims the priority of French Patent Application No. 0651913, filed May 24, 2006, and claims the benefit of U.S. Provisional Application No. 60/814,530, filed Jun. 19, 2006, the content of all of which is incorporated herein by reference.

The invention relates to a process for relaxing keratin fibres with a heating means and at least one cyclic or linear amide.

The relaxing process according to the invention is performed without using any reducing agent or lanthionizing agent. It does not include any reducing or lanthionization step.

According to the invention, the term "keratin fibres" means fibres of human or animal origin such as head hair, bodily hair, the eyelashes, wool, angora, cashmere or fur. Although the invention is not limited to particular keratin fibres, reference will nevertheless be made more particularly to head hair.

According to the invention, the term "relaxing" covers the relaxing, straightening or uncurling of Caucasian or African hair.

The term "heating means" means any means for heating keratin fibres to a temperature of at least 110° C., such as heating irons, for example flat or round irons, microwave generators or sources of infrared radiation.

Two techniques are used for permanently reshaping the hair. They are based on cleavage of the disulfide covalent bonds present in keratin (cystine):

the first consists, in a first stage, in performing this opening of the disulfide bonds using a composition containing a reducing agent, and then, after having preferably rinsed the hair, in reconstituting the said disulfide bonds in a second stage, by applying to the hair, which has been placed under tension beforehand with rollers or the like or shaped or straightened out by other means, an oxidizing composition also known as a fixer, so as to give the head of hair the desired shape. This technique makes it possible either to make the hair wavy or to relax it, uncurl it or straighten it out;

the second consists in performing a "lanthionization" operation using a composition containing a base belonging to the hydroxide family. This leads to replacement of the disulfide bonds (—CH2—S—S—CH2—) with lanthionine bonds (—CH2—S—CH2—). This lanthionization operation involves two consecutive chemical reactions:

the first reaction consists of a beta-elimination on cystine brought about by a hydroxide ion, leading to the cleavage of this bond and to the formation of dehydroalanine:

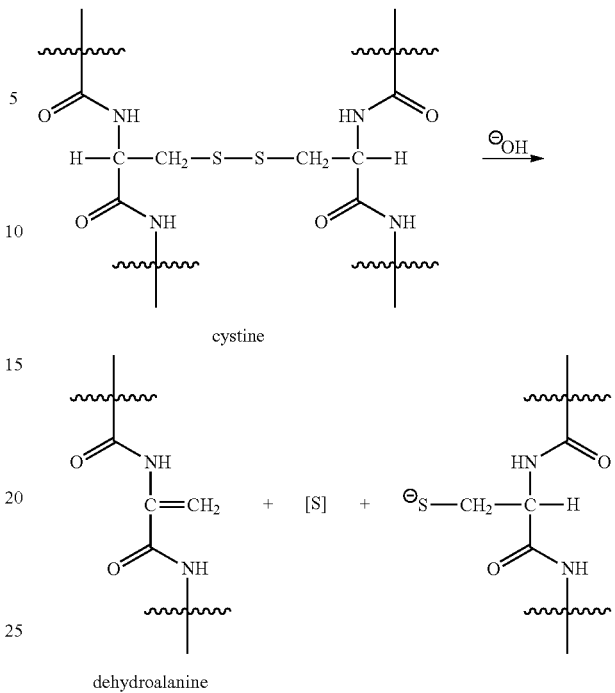

the second reaction is a reaction of dehydroalanine with a thiol group. Specifically, the double bond of the dehydroalanine formed is a reactive double bond. It can react with the thiol group of the cysteine residue that has been released to form a new bond referred as a lanthionine bridge or bond or residue.

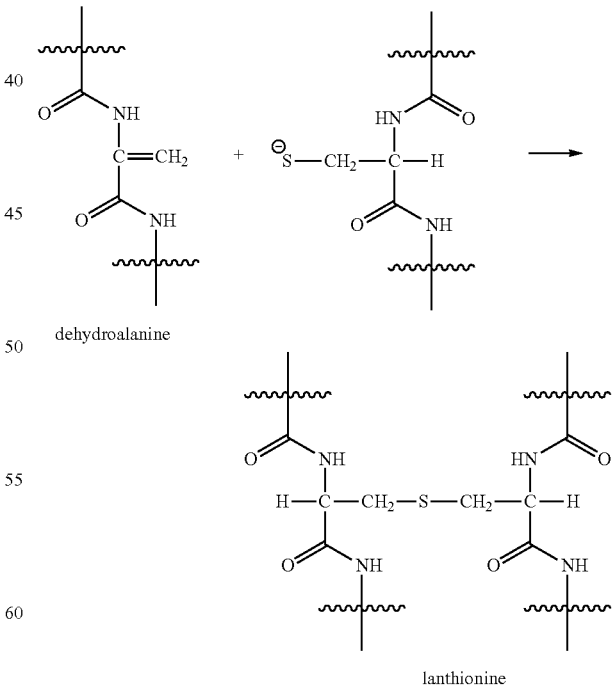

Relative to the first technique using a reducing agent, this lanthionization technique does not require a fixing step, since the formation of the lanthionine bridges is irreversible.

It is thus performed in a single step and makes it possible either to make the hair wavy, or to relax it, uncurl or straighten it out. However, it is mainly used for relaxing naturally curly hair.

For the first technique, the reducing compositions generally used for the first step of a permanent-waving or hair-relaxing operation contain thiols, sulfites or bisulfites as reducing agent. These agents are generally used in essentially aqueous medium at concentrations of between 0.5 and 1 M to obtain good opening of the disulfide bonds. Among the thiols, those commonly used are thioglycolic acid, cysteamine, glyceryl monothioglycolate, thiolactic acid and cysteine. Thioglycolic acid is particularly efficient at reducing the disulfide bonds of keratin at alkaline pH, especially in the form of ammonium thioglycolate, and constitutes the product most frequently used in permanent waving ("hair waving"). It has been found, however, that thioglycolic acid must be used in sufficiently basic medium (in practice at a pH of between 8.5 and 9.5) if curling of satisfactory intensity is to be obtained. Besides the drawback of releasing an unpleasant odour requiring the use of more or less efficient fragrances to mask the odours, the use of a thiol at alkaline pH also results in degradation of the fibre and most particularly in impairment of artificial colorations.

Sulfites or bisulfites are mainly used for relaxing the hair. They have drawbacks similar to those of thiols, with lower efficacy.

Thiols and sulfites (or bisulfites) also have the drawback of having poor stability in aqueous solution.

In general, the durability of the reshaping effects obtained with thiols and sulfites by reduction of disulfides following by fixing is judged to be very much lower than that which may be obtained via the lanthionization technique.

For the second technique, the compositions generally used to perform lanthionization contain as base a hydroxide such as sodium hydroxide, guanidinium hydroxide or lithium hydroxide. These lanthionization active agents, which allow opening of the disulfide bonds via a beta-elimination mechanism, are generally used as a water-oil emulsion at concentrations of between 0.4 and 0.6 M, by leaving them to act generally for 10 to 15 minutes at room temperature. Sodium hydroxide remains the agent most frequently used. Guanidinium hydroxide is now the preferred compound for many compositions. These two hydroxides, sodium hydroxide and guanidinium hydroxide, are the two main agents used for the relaxing or uncurling of naturally curly hair. They have several advantages over ammonium thioglycolate and sulfites, in particular the absence of unpleasant odour, the fact that only one operating step is required (shorter treatment time) and much greater durability and efficacy of reshaping of the hair.

However, these hydroxides have the major drawback of being caustic. This causticity affects the scalp by causing irritation, which is occasionally severe. This may be partially remedied by applying beforehand to the scalp fatty protective cream often referred to as a "base" or "base cream", the word "base" in this case not having the meaning of a basic agent in the chemical sense. When the protective cream is combined with the hydroxide in a single composition, it is generally referred to as "no-base", as opposed to the above name. This "no-base" technique is preferred.

The causticity of hydroxides also affects the state of the hair by firstly giving it a coarse feel and secondly making it much more brittle, this brittleness possibly going as far as crumbling or breaking or even dissolution of the hair if the treatment is prolonged. In certain cases, hydroxides also cause decoloration of the natural colour of the hair.

Formulations containing sodium hydroxide are generally referred to as "lye relaxers" and those not containing it are referred as "no-lye relaxers".

The main relaxing formulations known as "no-lye" relaxers use guanidinium hydroxide. Since guanidinium hydroxide is unstable, it is generated at the time of use by mixing guanidinium carbonate and a source of sparingly soluble hydroxide such as calcium hydroxide. The reaction between these two compounds leads to the formation of guanidinium hydroxide and calcium carbonate, which precipitates in the composition. The presence of this precipitate makes the final rinsing of the hair much more difficult and leaves mineral particles on the hair and the scalp, which give it a coarse feel and an unaesthetic appearance resembling dandruff. The recent success of guanidinium hydroxide ("no-lye") over sodium hydroxide ("lye") appears to arise from better relaxing efficacy and better skin tolerance. However, these techniques using bases of the hydroxide family remain very aggressive to the hair and the scalp and require very strict control of the duration of application to avoid excessive irritation and impairment of the hair that may go as far as breakage. This aggressiveness arising from the causticity of hydroxides is justification for not using these hair lanthionization compositions for permanent waving (hair waving), but solely for hair straightening or hair relaxing.

Furthermore, hydroxides are known to be good agents for hydrolysing amide functions (cf. for example March's Advanced Organic Chemistry, 5th edition, Wiley Interscience, New York, "Hydrolysis of Amides" page 474 et seq.), which thus lead to cleavage of peptide bonds by direct nucleophilic attack. It is thus probable that the observed impairments of the hair and of keratin materials in the broad sense are largely due to partial hydrolysis of the amide bonds of keratin.

There is thus a real need for relaxing compositions that are markedly less aggressive to the hair.

Various studies have been conducted in order to overcome both the drawbacks of reducing agents (first technique) and/or those of hydroxides (second technique).

Thus, many reducing agents have been proposed to replace thioglycolic acid, but thioglycolic acid in the form of ammonium thioglycolate remains both the reference compound and the compound most widely used in cosmetic formulations, not only for shaping but also for straightening the hair.

It has also been proposed in numerous patents to combine common reducing agents (thiols, sulfites or bisulfites) with urea or alkyl ureas to reduce the irritation and damage caused to the hair, not only for shaping but also for relaxing. Mention will be made, for example, of:

patent application CA 1315204, which describes a composition containing ammonium thioglycolate (5.5-11.5%) and urea or a monoalkyl urea (1-3%) for shaping the hair, patent application U.S. Pat. No. 3,847,165, which describes a composition containing ammonium thioglycolate (1.2-1.4 M) and urea (2.0-2.7 M) for shaping the hair at an acidic pH, patent application NL 6410355, which describes a composition containing a sulfite (0.8-1.5 M) and urea (0.6-3.0 M) for shaping and relaxing the hair, patent application JP 2000/229 819, which describes a composition containing a sulfite or bisulfite (0.5-15%), urea (0.5-15%) and an alcohol (ethanol and/or isopropanol, 1-30%) for shaping and relaxing the hair.

It has also been proposed in numerous patents to combine hydroxides, serving as lanthionization active agent, with certain additives generally serving to protect the hair. Mention will be made, for example, of:
- patent application WO 2002/003 937, which describes a composition containing C3-C5 monosaccharides,
- patent application WO 2001/064 171, which describes a composition containing complexing agents,
- U.S. Pat. No. 5,641,477, which describes a composition containing a hydrogenated starch hydrolysate,
- patent application WO 02/085 317, which describes a composition containing organic nucleophiles that react during the second step with the dehydroalanine formed with hydroxides, to give new bridges.

Although all these proposals lead to more or less pronounced improvements, they are not able to sufficiently reduce the damage associated with the very causticity of hydroxides.

As indicated previously, the use of reducing agents leads to poor durability of the relaxing or straightening of the hair and the use of hydroxides, on account of their causticity, limits their use in the field of hair relaxing.

After considerable studies, it has now been discovered, entirely surprisingly and unexpectedly, that hair can be durably relaxed by combining the action of a cyclic or linear amide and of a means of heating to a temperature above 110° C. Excellent results in terms of relaxing, cosmetic properties of the hair and fibre integrity are thus obtained.

Without being bound by theory, the Applicant considers that there is a combined action, on the keratin fibres, of a cyclic or linear amide and of a heating means, which allows the fibres to be efficiently and durably relaxed.

The Applicant has found that it is possible to overcome the drawbacks of the prior art and to satisfy the abovementioned objectives by performing a process for relaxing keratin fibres, comprising:
- a step of applying to the keratin fibres a hair-relaxing composition containing at least one particular cyclic or linear amide, the pH of this composition being less than or equal to 9,
- a step of raising the temperature of the keratin fibres, using a heating means, to a temperature of between 110 and 250° C.

Thus, the invention relates to a process for relaxing keratin fibres, comprising:
(i) a step of applying to the keratin fibres a hair-relaxing composition containing at least one cyclic or linear amide, the pH of this composition being less than or equal to 9,
(ii) a step of raising the temperature of the keratin fibres, using a heating means, to a temperature of between 110 and 250° C.,
characterized in that:
(1) the cyclic amides correspond to the general formula (I):

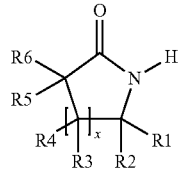

with
X=0 to 3
R1, R2, R3, R4, R5 and R6, which may be identical or different, possibly taking the following meaning:

H,
F,
linear or branched C1-C30 alkyl, possibly comprising one or more unsaturations,
  optionally interrupted with —O—, —S—, —NR7-, —C(O)—, —OC(O)—, —C(O)O—, —C(O)NR7-, —NR7C(O)—, —OC(O)NR7-, —NR7C(O)O—, —NR7C(O)NR8-, —NR7SO2-, —NR7SO2NR8-, —SO2NR7-, —OSO2-, —C(S)NR7-, —NR7C(S)—,
  optionally substituted with —OR7, —SR7, —NR7R8, —C(O)R7, —OC(O)R7, —C(O)OR7, —C(O)NR7R8, —NR7C(O)R8, —OC(O)NR7R8, —NR7C(O)OR8, —NR7C(O)NR8R9, —NR7SO2R8, —NR7SO2NR8R9, —SO2NR7R8, —OSO2R7, —C(S)NR7R8, —NR7C(S)R8, an aromatic or non-aromatic, heterocyclic or non-heterocyclic ring, possibly containing 3 to 10 atoms,
—OR7, —SR7, —NR7R8, —C(O)R7, —OC(O)R7, —C(O)OR7, —C(O)NR7R8, —NR7C(O)R8, —OC(O)NR7R8, —NR7C(O)OR8, —NR7C(O)NR8R9, —NR7SO2R8, —NR7SO2NR8R9, —SO2NR7R8, —C(S)NR7R8, —NR7C(S)R8,
an aromatic or non-aromatic, heterocyclic or non-heterocyclic ring, possibly containing 3 to 10 atoms, which is optionally substituted,
R1, R2, R3, R4, R5 and R6 possibly forming in pairs, with the carbon atoms to which they are attached, a (hetero)cycle of 3 to 7 atoms, optionally interrupted with O, S, N, —C(O)—, —C(O)O—, —C(O)NR7-,
R1R2, R3R4, and R5R6 possibly being combined in pairs to form an oxo function,
R7, R8 and R9, which may be identical or different, possibly taking the following meaning:
  H, F, optionally substituted linear or branched C1-C30 alkyl, possibly containing one or more unsaturations,
  one of the 20 natural N-branched amino acids, C-protected with standard protecting groups or one of the 20 natural C-branched amino acids, N-protected with standard protecting groups,
  an aromatic or non-aromatic, heterocyclic or non-heterocyclic ring, possibly containing 3 to 10 atoms,
and also the stereoisomers, organic or mineral salts and solvates thereof,
(2) the linear amides correspond to the general formula (II):

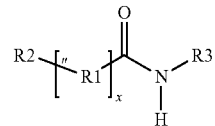

with
X=0 or 1
if X=0
R2 possibly taking the following meaning:
  H
  F, Cl
  an optionally substituted, heterocyclic or non-heterocyclic, aromatic or non-aromatic ring, which may contain 3 to 10 atoms,
  —OR7, —SR7, —C(O)R7, —OC(O)R7, —C(O)OR7, —C(O)NR7R8, —OC(O)NR7R8, —SO2NR7R8, —C(S)NR7R8, R3 possibly taking the following meaning:

H, except if R2 is 3-pyridine
linear or branched C1-C30 alkyl, possibly comprising one or more unsaturations,
  optionally interrupted with —O—, —S—, —NR7-, —C(O)—, —OC(O)—, —C(O)O—, —C(O)NR7-, —NR7C(O)—, —OC(O)NR7-, —NR7C(O)O—, —NR7C(O)NR8-, —NR7SO2-, —NR7SO2NR8-, —SO2NR7-, —OSO2-, —C(S)NR7-, —NR7C(S)—,
  optionally substituted with:
    F, Cl
    —OR7, —SR7, —NR7R8, —C(O)R7, —OC(O)R7, —C(O)OR7, —C(O)NR7R8, —NR7C(O)R8, —OC(O)NR7R8, —NR7C(O)OR8, —NR7C(O)NR8R9, —NR7SO2R8, —NR7SO2NR8R9, —SO2NR7R8, —OSO2R7, —C(S)NR7R8, —NR7C(S)R8
    a heterocyclic or non-heterocyclic, aromatic or non-aromatic ring, possibly containing 3 to 10 atoms,
R7, R8 and R9, which may be identical or different, possibly taking the following meaning:
  H,
  linear or branched C1-C30 alkyl, possibly comprising one or more unsaturations,
  one of the 20 natural N-branched amino acids, C-protected with standard protecting groups, or one of the 20 natural C-branched amino acids, N-protected with standard protecting groups,
  a heterocyclic or non-heterocyclic, aromatic or non-aromatic ring, possibly containing 3 to 10 atoms,
if X=1
R1 possibly taking the following meaning:
linear or branched C1-C30 alkylene, possibly containing one or more unsaturations,
  optionally interrupted with —O—, —S—, —NR7-, —C(O)—, —OC(O)—, —C(O)O—, —C(O)NR7-, —NR7C(O)—, —OC(O)NR7-, —NR7C(O)O—, —NR7C(O)NR8-, —NR7SO2-, —NR7SO2NR8-, —SO2NR7-, —OSO2-, —C(S)NR7-, —NR7C(S)—,
  optionally substituted with:
    F, Cl
    —OR7, —SR7, —NR7R8, —C(O)R7, —OC(O)R7, —C(O)OR7, —C(O)NR7R8, —NR7C(O)R8, —OC(O)NR7R8, —NR7C(O)OR8, —NR7C(O)NR8R9, —NR7SO2R8, —NR7SO2NR8R9, —SO2NR7R8, —OSO2R7, —C(S)NR7R8, —NR7C(S)R8,
    an aromatic or non-aromatic, heterocyclic or non-heterocyclic ring, possibly containing 3 to 10 atoms, with the exception of hydroxyl or oxo substituents in a position alpha to the amide function
R2 possibly taking the following meaning:
  H
  F, Cl
  an aromatic or non-aromatic, heterocyclic or non-heterocyclic ring, which is optionally substituted, possibly containing 3 to 10 atoms,
  —OR7, —SR7, —NR7R8, —C(O)R7, —OC(O)R7, —C(O)OR7, —C(O)NR7R8, —NR7C(O)R8, —OC(O)NR7R8, —NR7C(O)OR8, —NR7C(O)NR8R9, —NR7SO2R8, —NR7SO2NR8R9, —SO2NR7R8, —C(S)NR7R8, —NR7C(S)R8

R3 possibly taking the following meaning:
  H
  linear or branched C1-C30 alkyl, possibly containing one or more unsaturations,
    optionally interrupted with —O—, —S—, —NR7-, —C(O)—, —OC(O)—, —C(O)O—, —C(O)NR7-, —NR7C(O)—, —OC(O)NR7-, —NR7C(O)O—, —NR7C(O)NR8-, —NR7SO2-, —NR7SO2NR8-, —SO2NR7-, —OSO2-, —C(S)NR7-, —NR7C(S)—,
    optionally substituted with:
      F, Cl
      —OR7, —SR7, —NR7R8, —C(O)R7, —OC(O)R7, —C(O)OR7, —C(O)NR7R8, —NR7C(O)R8, —OC(O)NR7R8, —NR7C(O)OR8, —NR7C(O)NR8R9, —NR7SO2R8, —NR7SO2NR8R9, —SO2NR7R8, —OSO2R7, —C(S)NR7R8, —NR7C(S)R8
      an aromatic or non-aromatic, heterocyclic or non-heterocyclic ring, possibly containing 3 to 10 atoms,
R7, R8 and R9, which may be identical or different, possibly taking the following meaning:
  H,
  linear or branched C1-C30 alkyl, possibly containing one or more unsaturations,
  one of the 20 natural N-branched amino acids, C-protected with standard protecting groups, or one of the 20 natural C-branched amino acids, N-protected with standard protecting groups,
  an aromatic or non-aromatic, heterocyclic or non-heterocyclic ring, possibly containing 3 to 10 atoms,
  if R2(R1)x represents a fatty acid-based saturated or unsaturated alkyl radical, this alkyl radical contains less than 16 carbon atoms,
and also the stereoisomers thereof and the organic or mineral salts and solvates thereof.

Preferably, if R2(R1)x represents a fatty acid-based saturated or unsaturated alkyl radical, this alkyl radical contains less than 9 carbon atoms.

Advantageously, the temperature is raised using a heating means to a temperature of between 120° C. and 220° C. and more advantageously between 140° C. and 220° C.

Preferably, the said composition is applied to wet keratin fibres.

A step intended to remove the excess composition, for example using a towel, may also be introduced between the step of applying the composition and the step of raising the temperature.

Preferred compounds of formula (I):
2-pyrrolidone
3-methyl-2-pyrrolidone
pyroglutamic acid
5-methyl-2-pyrrolidone
succinimide
α-methyl-α-phenylsuccinimide
ethyl pyroglutamate
2-oxo-4-phenylpyrrolidine-3-carboxylic acid
pyrrolidonyl-4-butyramide
5-(hydroxymethyl)-2-pyrrolidinone methyl pyroglutamate
ethyl 2-oxo-4-phenyl-3-pyrrolidinecarboxylate
4-(hydroxy)-4-methylpyrrolidin-2-one
4-fluoro-5-pyrrolidone-2-carboxylic acid
4,4-pentamethylene-2-pyrrolidinone
[(5-oxopyrrolidine-2-carbonyl)amino]acetic acid
2-[(5-oxopyrrolidine-2-carbonyl)amino]-3-phenylpropionic acid
5-methoxy-2-pyrrolidinone
2-azabicyclo[2.2.1]hept-5-en-3-one butyl 2-pyrrolidone-5-carboxylate
octyl 2-pyrrolidone-5-carboxylate
4-carbamoyl-2-[(5-oxopyrrolidine-2-carbonyl)amino]-butyric acid
4-hydroxy-2-pyrrolidinone
2-dimethylamino ethyl 5-oxopyrrolidine-2-carboxylate
3-(1H-indol-3-yl)-2-[(5-oxopyrrolidine-2-carbonyl)-amino] propionic acid
5-pyridin-3-ylpyrrolidin-2-one
2-azabicyclo[2.2.1]heptan-3-one
methyl 2-[3-(methoxymethyl)-5-oxo-2-pyrrolidinyl]-acetate
4-phenyl-2-pyrrolidinone
4-spiro-[3[(2-pyrrolidinone)]piperidine
(4-[3-(cyclopentyloxy)-4-methoxyphenyl]pyrrolidin-2-one
2-amino-5-oxo-5-(5-oxopyrrolidin-2-yl)pentanoic acid
2-(2,5-dioxopyrrolidin-3-ylsulfanyl)nicotinic acid
3-hydroxynorcotinine
3-benzyl-5-hydroxymethylpyrrolidin-2-one
ethyl 4-methylpyroglutamate
ethyl 4-ethylpyroglutamate
ethyl 4-isopropylpyroglutamate
ethyl 4-benzylpyroglutamate
3-ethyl-5-hydroxymethylpyrrolidin-2-one
5-hydroxymethyl-3-methylpyrrolidin-2-one
5-oxopyrrolidine-3-carboxylic acid
5-hydroxymethyl-3-isopropylpyrrolidin-2-one
5-hydroxymethylpyrrolidin-2-one
5-aminomethylpyrrolidin-2-one
ethyl 2-oxopyrrolidine-3-carboxylate
3-hydroxypyrrolidin-2-one
3-ethyl-4-methylpyrrolin-2-one
3,4-(1,3-propanediyl)-2-pyrrolidinone
δ-valerolactam
3-carbethoxy-2-piperidone
glutarimide
3,3-dimethylglutarimide
3-ethyl-3-methylglutarimide
6-methyl-2-piperidone
3-methylpiperidin-2-one
D-mannono-D-lactam
N-(2-aminoethyl)-2-oxopiperidine-3-carboxamide
4-phenyl-δ-valerolactam
3-amino-4-phenyl-δ-valerolactam
4-methyl-3-phenyl-δ-valerolactam
3-methyl-5-phenyl-δ-valerolactam
3-(2-isopropoxycarbonylethyl)-6-oxopiperidine-3-carboxylic acid
3-(2-benzylcarbamoylethyl)-6-oxopiperidine-3-carboxylic acid
methyl 2-oxopiperidine-3-carboxylate
3,4,5-trihydroxy-6-oxo-2-piperidinecarboxylic acid
2-piperidinone-6-carboxylic acid
5-hydroxypiperidin-2-one
ethyl 5-methyl-2-oxo-3-piperidinecarboxylate
6-oxopiperidine-2-carboxylic acid
4-hydroxypiperidin-2-one
2-azetidinone
ε-caprolactam
and the stereoisomers, organic or mineral salts and/or solvates thereof.
  Particularly preferred compounds of formula (I):
2-pyrrolidone
pyroglutamic acid
3-methyl-2-pyrrolidone
5-methyl-2-pyrrolidone
5-(hydroxymethyl)-2-pyrrolidinone
5-oxopyrrolidine-3-carboxylic acid
5-aminomethylpyrrolidin-2-one
4-hydroxy-2-pyrrolidinone
and the stereoisomers, organic or mineral salts and/or solvates thereof.
  Preferred compounds of formula (II):
acetamide
N-methylacetamide
propionamide
N-ethylacetamide
N-methylpropionamide
N-butyramide
N-(hydroxymethyl)acetamide
methoxyacetamide
hydracrylamide
2-mercaptoacetamide
acetoacetamide
N—(N-propyl)acetamide
N— ethylpropionamide
valeramide
malonamide
N-acetylethylenediamine
2-amino-N-ethylacetamide
N-acetylethanolamine
3-chloropropionamide glycinamide
N-(cyclopropylmethyl)acetamide
N-methylacetoacetamide
1-acetamidoacetone
N-methylvaleramide
N-butylacetamide
hexanamide
N-acetylglycinamide
succinamide
N-ethyl-2-methylaminoacetamide
N-acetylglycine
succinamic acid
methyl carbamoylacetate
N-(2-hydroxyethyl)propionamide
N1-(3-hydroxypropyl)acetamide
5-hydroxyvaleramide
3-amino-3-thioxopropanamide
O-(2-hydroxyethyl)glycolamide
3,4-dihydroxybutyramide
N-(2-chloroethyl)acetamide
N-(3-methylbutyl)acetamide
N-methylsuccinamic acid
ethyl carbamoylacetate
glycylglycine
asparagine
2-amino-N-(2-methoxyethyl)acetamide
2-(2-amino-2-oxoethoxy)acetic acid
2-phenylacetamide
pyridin-2-acetamide pyridin-4-acetamide
methyl sulfonylacetamide
4-aminobutyramide
5-acetaminomethyltetrazole
thiophen-2-acetamide
4-thiazoleacetamide
1-aminocyclopentanacetamide
2-piperazin-1-ylacetamide
N-octanamide
N,N'-diacetylethylenediamine
adipamide
2-morpholinoacetamide ethyl acetamidoacetate
4-acetamidobutyric acid
2-(acetylamino)ethyl acetate
N-(2-hydroxyethyl)acetoacetamide
isopropyl carbamoylacetate 2-amino-N-methylsuccinamic acid
glutamine
N-(2-methoxyethyl)-2-methylaminoacetamide
N-methyl-2-phenylacetamide
N-benzylacetamide
N-propylpyrrolidine-2-carboxamide
N-(tert-butyl)-1,2,3,4-tetrahydroisoquinoline-3-carboxamide
N,N-butylpropionamide
N-1,3,3-trimethylbutanamide
N-α-acetyl-L-lysine-N-methylamide
L-proline N-octylamide
and also the stereoisomers thereof and the organic or mineral salts and solvates thereof,
and also the following amino acids and derivatives:
AC-ALA-NHME
AC-β-ALA-OH
AC-β-ALA-OME
AC-GLY-NHME
AC-HIS-NHME
AC-ILE-NHME
AC-LEU-GLY-OH
AC-LEU-NHME
AC-LYS-NHME
AC-PHE-NHME
AC-SER-GLY-OH
AC-VAL-NHME
H-β-ALA-GLY-OH
H-β-ALA-NH2
H-GLY-β-ALA-OH
H-GLY-NHME
H-PRO-ALA-OH
H-PRO-ALA-OH
H-PRO-β-ALA-OH
H-PRO-GLY-NH2
H-PRO-GLY-OH
H-PRO-GLY-OH
H-PRO-ILE-OH
H-PRO-LEU-OH
H-PRO-NHCH3
H-PRO-NHET
H-PRO-SER-OH
H-PRO-VAL-OH
H-PRO-VAL-OH
SAR-GLY-OH
SAR-NH2
and also the stereoisomers thereof and the organic or mineral salts and solvates thereof.
Particularly preferred compounds of formula (II):
acetamide
N-methylacetamide
N-ethylacetamide
propionamide
N-ethylpropionamide
and also the stereoisomers thereof and the organic or mineral salts and solvates thereof.
Working Concentrations The working molar concentration is between 2 and 8 M and more advantageously between 4 and 8 M.

The working pH is preferably less than or equal to 7.

The compositions according to the invention are either in the form of an aqueous solution or in the form of a thickened cream so as to keep the hair as straight as possible. These creams are prepared in the form of "heavy" emulsions.

These compositions contain at least one cyclic amide of formula (I) and/or at least one linear amide of formula (II) and/or mixtures thereof in all proportions.

Advantageously, the compositions of the invention contain at least one cyclic or linear amide of formula (I) or (II) as sole hair-relaxing active agent.

For the purpose of improving the cosmetic properties of keratin fibres or to attenuate or avoid their degradation, the composition used according to the invention may also comprise one or more additional cosmetic active agents.

Generally, the said additional cosmetic active agent(s) represent(s) from 0.01% to 30% and preferably from 0.1% to 10% by weight relative to the total weight of the cosmetic composition.

Generally, the composition applied to the keratin fibres is applied in an amount of from 0.05 to 20 g and preferably from 0.1 to 10 g of composition per gram of dry keratin fibre.

After applying the composition, and before raising the temperature of the keratin fibres using a heating means, the said composition may be left to act, generally for 30 seconds to 60 minutes and preferably 5 to 45 minutes.

The process according to the invention includes, after the step of applying the composition, a step of raising the temperature of the keratin fibres, using a heating means, to a temperature of between 110° C. and 250° C.

Advantageously, an iron is used as heating means.

For the purposes of the present invention, the term "iron" means a device for heating keratin fibres that places the said fibres and the heating device in contact.

The end of the iron that comes into contact with the hair generally has two flat surfaces. These two flat surfaces may be metallic. They may be smooth or crinkled.

As examples of irons that may be used in the process according to the invention, mention may be made of flat irons of any type, and in particular, in a non-limiting manner, those described in patents U.S. Pat. Nos. 5,957,140 and 5,046,516.

The iron may be applied by successive separate touches of a few seconds, or by gradually moving or sliding it along the locks.

Preferably, in the process according to the invention, the iron is applied by continuous movement from the root to the end, in one or more passes.

The process according to the invention may also include an additional step of partial predrying of the keratin fibres before the step of raising the temperature, so as to avoid substantial evolution of steam that might burn the stylist's hands and the individual's scalp. This predrying step may take place, for example, using a hairdryer, a hood or alternatively by drying in the open air.

The invention also relates to a kit comprising at least:
one heating means that affords a temperature of between 110 and 250° C.,
one hair-relaxing composition containing at least one cyclic or linear amide of formula (I) or (II), the pH of this composition being less than or equal to 9.

Advantageously, in the kit, the hair-relaxing composition contains at least one cyclic or linear amide of formula (I) and/or (II) and/or mixtures thereof in all proportions as defined above.

The invention may be understood more clearly with the aid of the non-limiting examples that follow, which constitute preferential embodiments of the compositions according to the invention.

EXAMPLE 1

A simplified hair-relaxing composition is prepared, containing 2-pyrrolidone at a concentration of 8 M in water, as hair-relaxing active agent. This composition is applied to naturally curly African hair for 15 minutes at a temperature of 40° C., and the hair is then rapidly towel-dried.

Lock-by-lock straightening of the head of hair is then performed using a flat iron heated to 180° C., for 10 to 15 seconds. The hair is efficiently relaxed and feels soft.

EXAMPLE 2

A simplified hair-relaxing composition is prepared, containing 2-pyrrolidone at a concentration of 6 M in water, as hair-relaxing active agent. This composition is applied to naturally curly African hair for 25 minutes at a temperature of 40° C., and the hair is then rapidly towel-dried.

Lock-by-lock straightening of the head of hair is then performed using a flat iron heated to 180° C., for 10 to 15 seconds. The hair is efficiently relaxed and feels soft.

The invention claimed is:

1. A process for relaxing keratin fibers, comprising:
   applying to the keratin fibers a hair-relaxing composition comprising, as the sole hair-relaxing agent, at least one cyclic amide at a molar concentration ranging from 2 M to 8 M, wherein the pH of said composition is less than or equal to 9,
   heating the keratin fibers to a temperature ranging from 110° C. to 250° C.,
   wherein the at least one cyclic amide is chosen from:
     2-pyrrolidone,
     pyroglutamic acid,
     3-methyl-2-pyrrolidone,
     5-methyl-2-pyrrolidone,
     5-(hydroxymethyl)-2-pyrrolidinone,
     5-aminomethylpyrrolidin-2-one,
     4-hydroxy-2-pyrrolidinone, and
     the stereoisomers, organic or mineral salts, and/or solvates thereof;
   wherein the hair-relaxing composition does not comprise a reducing agent; and
   wherein the process does not comprise a reducing step.

2. The process according to claim 1, wherein the at least one cyclic amide is a solvate.

3. The process according to claim 1, wherein said keratin fibers are heated to a temperature ranging from 120° C. to 220° C.

4. The process according to claim 3, wherein said keratin fibers are heated to a temperature ranging from 140° C. to 220° C.

5. The process according to claim 1, wherein the composition is applied to wet keratin fibers.

6. The process according to claim 1, wherein the fibers are partially predried.

7. The process according to claim 1, wherein the molar concentration of the at least one cyclic amide ranges from 6 M to 8 M.

8. The process according to claim 1, wherein the molar concentration of the at least one cyclic amide ranges from 4 M to 8 M.

9. The process according to claim 1, wherein the pH of the composition is less than or equal to 7.

10. A process for relaxing keratin fibers, comprising:
    applying to the keratin fibers a hair-relaxing composition comprising, as the sole hair-relaxing agent, 2-pyrrolidone or organic or mineral salts thereof, wherein the pH of said composition is less than or equal to 9, and
    heating the keratin fibers to a temperature ranging from 110 to 250° C.;
    wherein the hair-relaxing composition does not comprise a reducing agent; and
    wherein the process does not comprise a reducing step.

* * * * *